(12) United States Patent
Gabbay

(10) Patent No.: US 7,374,573 B2
(45) Date of Patent: *May 20, 2008

(54) SYSTEM AND METHOD FOR IMPROVING VENTRICULAR FUNCTION

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

This patent is subject to a terminal disclaimer.

(21) Appl. No.: 10/837,944

(22) Filed: May 3, 2004

(65) Prior Publication Data

US 2005/0246013 A1 Nov. 3, 2005

(51) Int. Cl.
*A61F 2/02* (2006.01)
(52) U.S. Cl. ..................................... 623/3.12
(58) Field of Classification Search ................. 623/2.1, 623/2.13, 23.65, 23.64, 3.1, 3.16
See application file for complete search history.

(56) References Cited

U.S. PATENT DOCUMENTS

| 4,976,735 | A | * | 12/1990 | Griffith et al. | 623/23.65 |
| 5,509,930 | A | | 4/1996 | Love | |
| 5,545,215 | A | | 8/1996 | Duran | |
| 6,090,140 | A | * | 7/2000 | Gabbay | 623/2.1 |
| 6,517,576 | B2 | * | 2/2003 | Gabbay | 623/2.14 |
| 2002/0036220 | A1 | * | 3/2002 | Gabbay | 224/191 |
| 2002/0143393 | A1 | * | 10/2002 | Cox | 623/2.12 |

FOREIGN PATENT DOCUMENTS

| WO | WO2004/108191 | * | 12/2004 |
| WO | PCT/US2005/023460 | | 6/2005 |

OTHER PUBLICATIONS

N. Radovanovi, et al., "Surgical Treatment Of Heart Failure", CTT Cardiothoracic Techniques and Technologies X, (date unknown), p. 58.
Charles Moore, et al., "Surgical Ventricular Restoration In End-Stage Ischemic Dilated Cardiomyopathy Patents", CTT 2004 Cardiothoracic Techniques and Technologies X, (date unknown), p. 157.
David A. Kass, M.D., "Ventriculectomy. A Direct Application of Laplace's Law", Arquivos Brasileiros de Cardiologia 67(6):, 1996, pp. 1-2.
Lisa A. Mendes, M.D., et al., "Ventricular Remodeling in Active Myocarditis", www.Medscape.com, 1999, pp. 1-8.
Martin St. John Sutton, FRCP, "Left Ventricular Remodeling And Synchronized Biventricular Pacing In Advanced Heart Failure", www.cardiologyrounds.org, Oct. 2003, vol. 7, Issue 8.

* cited by examiner

*Primary Examiner*—Corrine McDermott
*Assistant Examiner*—David A. Izquierdo
(74) *Attorney, Agent, or Firm*—Tarolli, Sundheim, Covell & Tummino LLP

(57) ABSTRACT

An approach is disclosed for improving ventricular function of a patient's heart. According to one embodiment, the system includes a pouch that defines a chamber dimensioned and configured to simulate at least a portion of a heart chamber. The pouch has a sidewall portion extending from an inflow annulus and terminating in a closed distal end spaced apart from the inflow annulus. A generally cylindrical outflow portion extends from the sidewall portion of the pouch and terminating in an outflow annulus thereof to provide for flow of fluid from the chamber through the outflow annulus. A valve is operatively associated with the inflow annulus of the pouch to provide for substantially unidirectional flow of fluid through the inflow annulus and into the chamber.

5 Claims, 3 Drawing Sheets

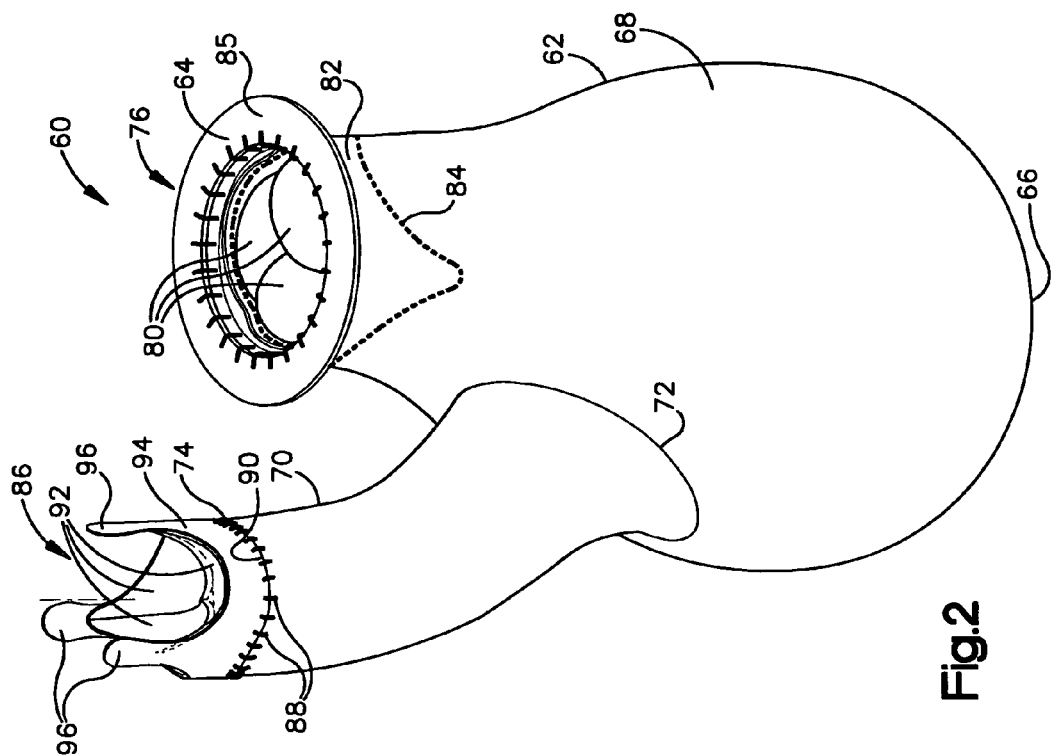
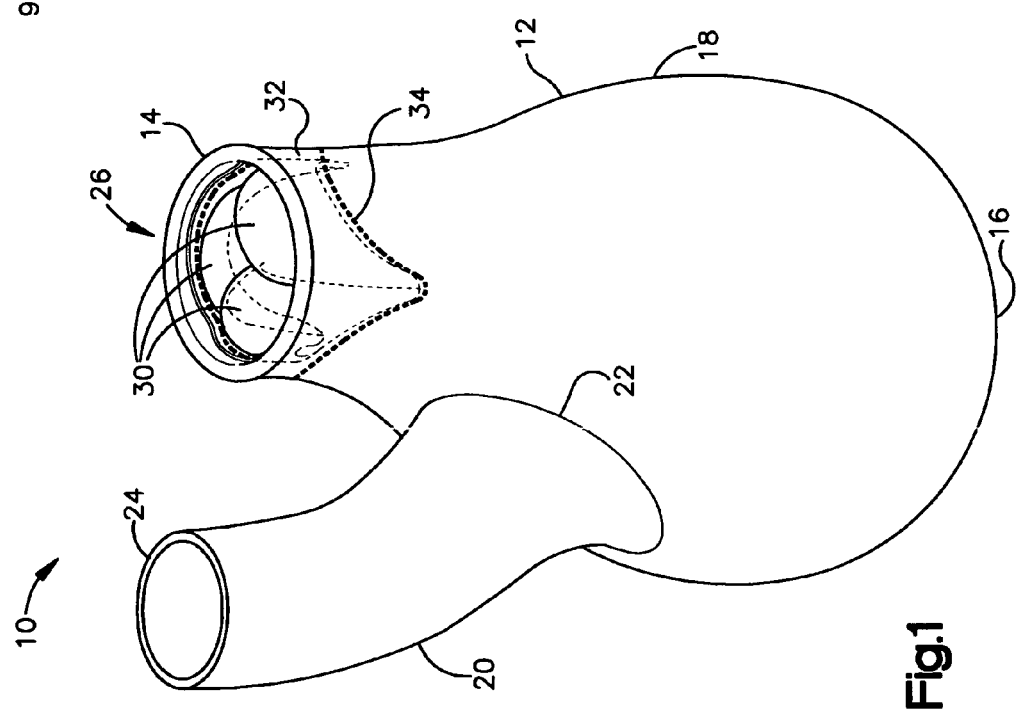

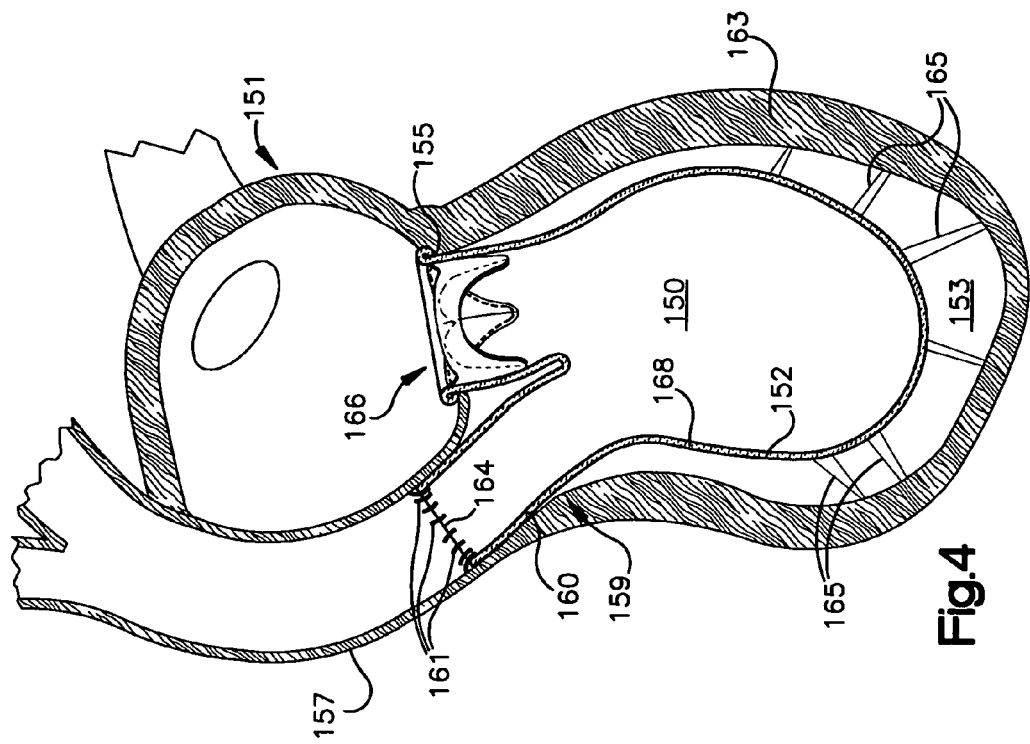
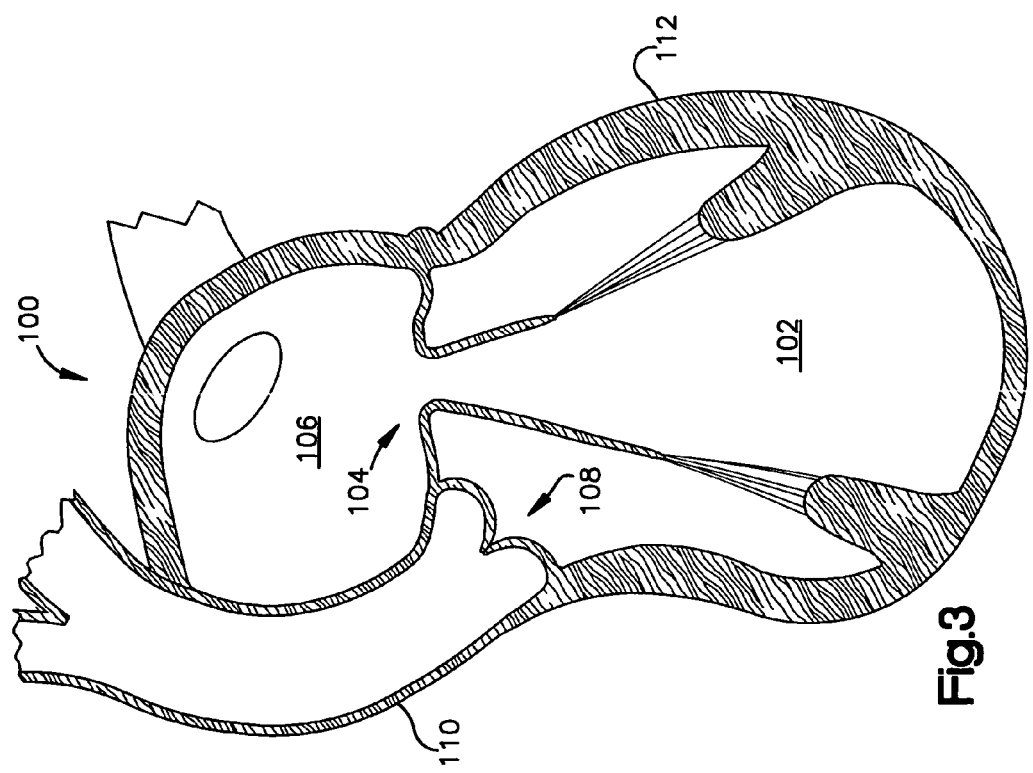

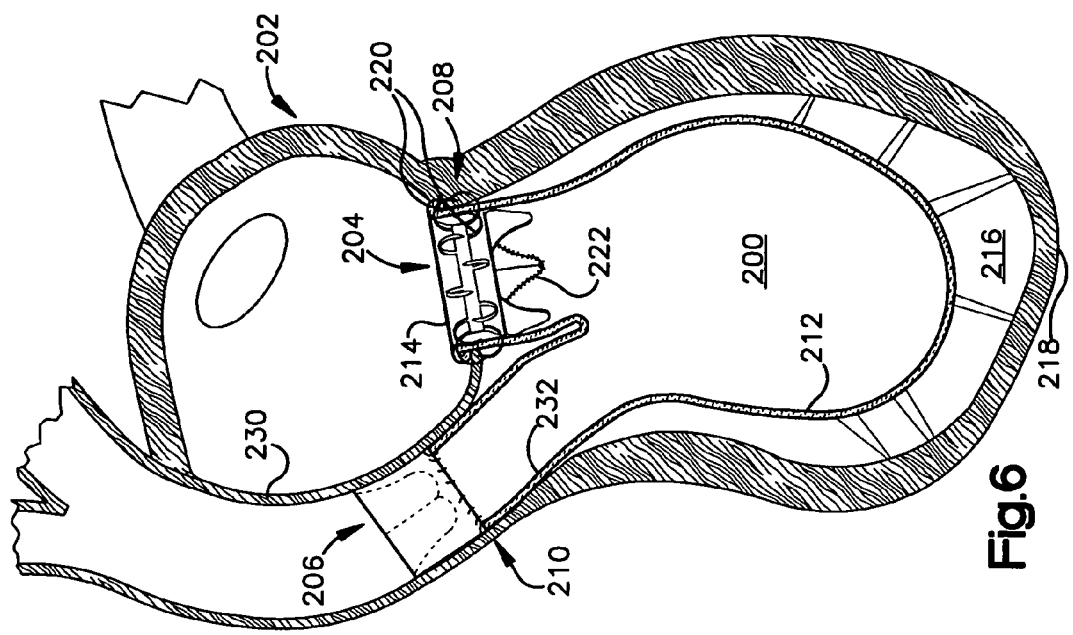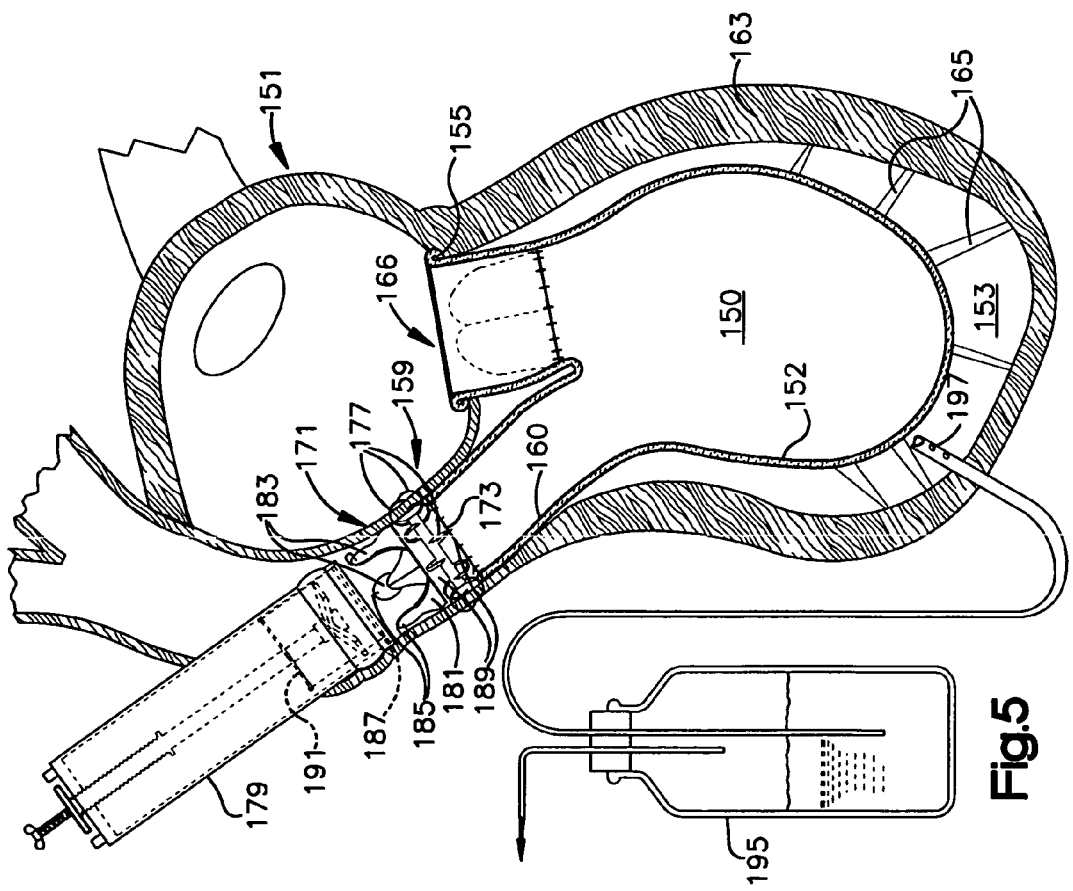

SYSTEM AND METHOD FOR IMPROVING VENTRICULAR FUNCTION

TECHNICAL FIELD

The present invention relates to the heart, and more particularly to a system and method for improving ventricular function.

BACKGROUND OF THE INVENTION

Dilated cardiomyopathy is a condition of the heart in which ventricles one or more become too large. Dilated cardiomyopathy occurs as a consequence of many different disease processes that impair myocardial function, such as coronary artery disease and hypertension. As a consequence of the left ventricle enlarging, for example, the ventricles do not contract with as much strength, and cardiac output is diminished. The resulting increase in pulmonary venous pressure and reduction in cardiac output can lead to congestive heart failure. Dilated cardiomyopathy can also result in enlargement of the mitral annulus and left ventricular cavity, which further produces mitral valvular insufficiency. This in turn, causes volume overload that exacerbates the myopathy, often leading to progressive enlargement and worsening regurgitation of the mitral valve.

A dilated ventricle requires more energy to pump the same amount of blood as compared to the heart of normal size. The relationship between cardiac anatomy and pressure has been quantified by La Place's law. Generally, La Place's law describes the relationship between the tension in the walls as a function of the transmural pressure difference, the radius, and the thickness of a vessel wall, as follows:

$T=(P*R)/M$, which solving for P reduces to:

$P=(T*M)/R$ where T is the tension in the walls, P is the pressure difference across the wall, R is the radius of the cylinder, and M is the thickness of the wall. Therefore to create the same pressure (P) during ejection of the blood, much larger wall tension (T) has to be developed by increase exertion of the cardiac muscle. Such pressure further is inversely proportional to the radius of the cylinder (e.g., the ventricle).

Various treatments exist for patients having dilated cardiomyopathy. One approach is to perform a heart transplant procedure. This is an extraordinary measure, usually implemented as a last resort due to the risks involved.

Another approach employs a surgical procedure, called ventricular remodeling, to improve the function of dilated, failing hearts. Ventricular remodeling (sometimes referred to as the Batista procedure) involves removing a viable portion of the enlarged left ventricle and repairing the resultant mitral regurgitation with a valve ring. This procedure attempts to augment systemic blood flow through improvement in the mechanical function of the left ventricle by restoring its chamber to optimal size. In most cases, partial left ventriculectomy is accompanied by mitral valve repair. With respect to La Place's law, a goal of ventriculectomy is to reduce the radius so that more pressure can be generated with less energy and less stress exertion by the patient's cardiac muscle.

SUMMARY

One aspect of the present invention provides a system for improving operation of a heart. The system includes a pouch that defines a chamber dimensioned and configured to simulate at least a portion of a heart chamber. The pouch has a sidewall portion extending from an inflow annulus and terminating in a closed distal end spaced apart from the inflow annulus. A generally cylindrical outflow portion extends from the sidewall portion of the pouch and terminating in an outflow annulus thereof to provide for flow of fluid from the chamber through the outflow annulus. A valve is operatively associated with the inflow annulus of the pouch to provide for substantially unidirectional flow of fluid through the inflow annulus and into the chamber.

Another aspect of the present invention provides a system for improving ventricular function that includes a pouch located within a ventricle of a patient's heart. The pouch is fluidly connected between a first valve at a mitral position of the patient's heart and a second valve in an aortic position of the patient's heart. The pouch is configured to limit a volume of blood within the ventricle.

Still another aspect of the present invention provides a system for improving ventricular function of a patient's heart, which includes: means for limiting a volume of blood received within an enlarged ventricle of the patient's heart; means for providing for substantially unidirectional flow of blood into the means for limiting; and means for providing for substantially unidirectional flow of blood out of the means for limiting into an aorta of the patient's heart.

Yet another aspect of the present invention provides a method for improving ventricular function of a heart. The method includes implanting a pouch in a ventricle, the pouch including an inflow annulus. An inflow valve is mounted associated with the inflow annulus of the pouch at a mitral position to provide for substantially unidirectional flow of blood through the inflow valve and into the implanted pouch. An end portion of a generally cylindrical member is secured at an aortic annulus. The generally cylindrical member extends from a sidewall of the pouch and terminates in the end portion to provide fluid communication from within the pouch into an aorta.

BRIEF DESCRIPTION OF THE DRAWINGS

FIG. 1 depicts an example of a system for improving ventricular function according to an aspect of the present invention.

FIG. 2 depicts an example of another system for improving ventricular function according to an aspect of the present invention.

FIG. 3 is a cross-sectional view of a heart illustrating a condition of dilated cardiomyopathy.

FIG. 4 illustrates a system for improving ventricular function implanted in a left ventricle according to an aspect of the present invention.

FIG. 5 depicts an example of another system for improving ventricular operation implanted in a ventricle in combination with an aortic valve according to an aspect of the present invention.

FIG. 6 depicts an example of another system for improving ventricular function implanted in a ventricle in combination with an aortic valve according to an aspect of the present invention.

DETAILED DESCRIPTION

FIG. 1 depicts an example of a system 10 for improving ventricular function of a heart. The system 10 includes an enclosure or pouch 12 that is dimensioned and configured to simulate at least a portion of a normal heart chamber. The pouch 12 includes an inflow annulus 14 spaced apart from a distal closed end 16 by a generally cylindrical sidewall 18. In the example of FIG. 1, the sidewall 18 of the pouch 12 has a generally pear-shaped contour, in which the portion of the sidewall 18 proximal the inflow annulus 14 has a reduced diameter relative to an intermediate portion thereof proximal the distal end 16.

A generally cylindrical outflow portion (e.g., a tubular branch) 20 extends from the sidewall 18 of the enclosure 12. The outflow portion 20 extends longitudinally from a first end 22 and terminates in an outflow end 24 that is spaced apart from the first end 22 by a generally cylindrical sidewall thereof. The first end 22 can be attached to the sidewall 18. For instance, the first end 22 can be connected to the sidewall 18 via a continuous suture to couple the outflow portion 20 with the sidewall portion such that fluid (e.g., blood) can flow from the chamber defined by the pouch 12 through the outflow portion 20. Alternatively, the first end 22 can be formed integral with the sidewall 18.

The system 10 also includes a valve 26 operatively associated with the inflow annulus 14. The valve 26 is configured to provide for substantially unidirectional flow of blood through the valve into the chamber defined by the pouch 12. For example, when the system 10 is mounted in a left ventricle, blood will flow from the left atrium through the valve 26 and into the chamber that defines a volume of the pouch 12.

Those skilled in the art will understand and appreciate that practically any type of prosthetic valve 26 can be utilized to provide for the unidirectional flow of blood into the chamber. For example, the valve 26 can be implemented as a mechanical heart valve prosthesis (e.g., a disc valve, ball-check valve, bileaflet valve), a biological heart valve prosthesis (homograft, autograft, bovine or porcine pericardial valve), or a bio-mechanical heart valve prosthesis (comprising a combination of mechanical valve and natural tissue materials), any of which can include natural and/or synthetic materials. Additionally, the valve 26 can be a stented valve or an unstented valve.

In the example of FIG. 1, the valve 26 is depicted as a biological heart valve prosthesis that is mounted at the annulus 14, such as by suturing an inflow annulus of the valve 26 to the annulus 14 of the system 10. The valve 26 can include one or more leaflets (typically two or three) or other movable members adapted to provide for desired unidirectional flow of blood through the valve and into the chamber of the pouch 12.

When a biological heart valve prosthesis is utilized to provide the valve 26, the valve typically includes two or more leaflets 30 movable relative to the annulus 14 to provide for the desired unidirectional flow of blood into the pouch 12. The leaflets 30 are mounted for movement within the inflow portion of the pouch 12, namely near the annulus 14. In the illustrated embodiment of FIG. 1, the leaflets 30 are mounted relative to a sidewall valve portion 32 of a previously harvested heart valve, which has been treated to improve its biocompatibility and mounted within a stent. The inflow end of the valve 26 is sutured to the inflow annulus 14 of the pouch 12, such as by sewing (or otherwise affixing) a sewing ring thereof relative to the annulus 14. An outflow end of the valve wall portion 32 of the valve 26 can be sewn by sutures 34 to the sidewall 18 of the pouch 12.

The pouch 12 can be formed of a biological tissue material, such as previously harvested animal pericardium, although other natural tissue materials also can be utilized (e.g., duramatter, collagen, and the like). The pericardium sheet or sheets utilized to form the pouch 12 has opposed interior/exterior side surfaces. According to one aspect of the present invention, the pericardial sheet(s) are oriented so that a rougher of the opposed side surfaces forms the interior sidewall portion of the chamber. The rougher surface facilitates formation of endothelium along the interior of the sidewall 18 thereby improving biocompatibility of the system 10.

By way of further illustration, the pouch 12 may be formed from one or more sheets of a NO-REACT® tissue product, which is commercially available from Shelhigh, Inc., of Millburn, N.J. as well as from distributors worldwide. The NO-REACT® tissue products help improve the biocompatibility of the system 10, thereby mitigating the likelihood of a patient rejecting the system. The NO-REACT® tissue also resists calcification when implanted. Those skilled in the art will appreciate various other materials that could be utilized to form the pouch 12, including collagen impregnated cloth (e.g., Dacron) as well as other biocompatible materials (natural or synthetic). The NO-REACT® tissue products further have been shown to facilitate growth of endothelium after being implanted.

FIG. 2 depicts an example of another system 60 that can be utilized to improve ventricular function according to an aspect of the present invention. The system 60 is substantially similar to that shown and described in FIG. 1. Accordingly, the reference numbers used in FIG. 2 are the same, increased by adding 50, as utilized to identify the corresponding parts previously identified in FIG. 1.

Briefly stated, the system 60 includes a pouch 62 dimensioned and configured to simulate at least a portion of a heart chamber, such as a ventricle. The pouch 62 includes an inflow annulus 64 spaced apart from a closed distal end 66 by a generally cylindrical (e.g., pear-shaped) sidewall 68. A generally cylindrical outflow portion 70 extends from the sidewall 68, which is configured for providing a fluid path from the interior of the pouch 62 to an aorta. The outflow portion 70 can be configured as a length of a generally cylindrical tissue that extends from a first end 72 connected to the sidewall 68 and terminates in a second end spaced 74 apart from the first end.

The system 60 also includes an inflow valve 76 at the inflow annulus 64, which provides for substantially unidirectional flow of blood into the chamber defined by the pouch 62. Various types and configurations of valves could be employed to provide the valve 76, such as mentioned herein. In the example of FIG. 2, the valve is depicted as a biological heart valve prosthesis having a plurality of leaflets 80 positioned for movement relative to an associated sidewall portion 82. An outflow end 84 of the valve 76 is attached at the inflow annulus 64 of the pouch 62 and extends into the pouch. The outflow end 84 can be sutured to the pouch 62. A sewing ring 85 can be provided at the inflow end of the valve 76 to facilitate its attachment at a mitral annulus of a patient's heart.

In the example of FIG. 2, an outflow valve 86 is also mounted at the outflow end 74 of the outflow portion 70. For example, the valve 86 can be attached to the outflow end 74 by sutures 88. While an inflow end 90 of the valve 86 is illustrated as being anastomosed to the inflow end 74 of the outflow portion 70, it will be understood and appreciated that, alternatively, an inflow extension of the valve 86 or the sidewall of the outflow portion 70 can be an overlapping relationship relative to the other. As still another alternative, the valve 86 can be integrally formed with the outflow portion 70.

In the example of FIG. 2, the valve 86 is illustrated as a biological heart valve prosthesis. The valve 86 thus includes a plurality of leaflets 92 positioned for movement within a corresponding sidewall portion 94 of the valve 86 to provide for substantially unidirectional flow of blood axially through the valve 86, as provided from the pouch 62. The valve 86 can be stented or unstented. The plurality of corresponding outflow extensions 96 are positioned at respective commissures of the valve 86 to facilitate its attachment and to maintain the valve at the aortic position of a patient's heart.

While the valve 86 is illustrated as a biological heart valve prosthesis, those skilled in the art will understand and appreciate that any type of valve can be utilized at the outflow annulus 74. By way of example, the valve 86 can be implemented as a mechanical heart valve, a biological heart valve or a bio-mechanical heart valve prosthesis. The valve 86 can be the same or a different type of valve from that utilized for the valve 76. Additionally, while the valve 86 is depicted as attached at the outflow annulus 74, the valve could be attached proximal the first end 72 or any where between the ends 72 and 74. It is to be appreciated that the valve 86 can be attached to the outflow portion 70 (e.g. through the aorta) after the other parts of the system 60 have been implanted.

FIG. 3 depicts an example of a heart 100 in which a left ventricle 102 is severely dilated, such as in the case of dilated cardiomyopathy. As a result of the dilated left ventricle 102, a mitral valve 104 can severely prolapse, such that the mitral valve 104 is unable to provide for desired unidirectional flow of blood from the left atrium 106 to the left ventricle 102.

In the example of FIG. 3, the aortic valve 108 appears intact and sufficient, although in many cases, the aortic valve may also be defective. The aortic valve 108, when operating properly, provides for a substantially unidirectional flow of blood from the left ventricle 102 into the aorta 110. As a result of the dilation of the left ventricle 102, however, associated cardiac muscle 112 of the heart 100 is required to expend greater energy to pump the same amount of blood in the absence of such dilation. The extra exertion can be described according to the well-know La Place's law, such as mentioned in the Background section.

FIG. 4 illustrates an example of a system 150 for improving ventricular function that has been implanted in a heart 151. The system 150 is substantially similar to the system shown and described with respect to FIG. 1, and reference numbers, increased by adding 140, refer to corresponding parts of the system 10 previously identified with respect to FIG. 1. Briefly stated, the system 150 includes a pouch 152 dimensioned and configured to simulate at least a portion of a properly functioning ventricle. Thus, by positioning the system 150 in the ventricle 153 of the heart 151, as shown in FIG. 4, ventricular function can be substantially improved (when compared to the dilated heart of FIG. 3). The pouch 152 can be generally pear-shaped extending from a valve 166 attached at a mitral annulus 155 of the heart 151.

A generally cylindrical outflow portion 160 extends from the sidewall 168 of the pouch 152 to fluidly connect the pouch with the aorta 157. As shown, the outflow end of the tubular brands 160 can be attached to the aorta 157 near the aortic annulus 159, such as by sutures 161. Prior to inserting the outflow portion 160 into the aorta 157, the patient's native aortic valve can be removed and the outflow annulus of the outflow portion can be positioned relative to the aortic annulus 159. Alternatively, it may also be possible to connect the outflow portion 160 of the system 150 to the patient's native aortic valve, thereby leaving the patient's valve intact. A more likely scenario, however, is that the aortic valve will be removed and replaced by a heart valve prosthesis. The length of the outflow portion 160 may also but cut to a desired length, and then sutured to the base of the aorta 157. This part of the process can be performed through an incision made in the aorta 157.

The valve 166 thus provides for substantially unidirectional flow of blood into from the atrium into the chamber defined by the pouch 152. Various types and configurations of valves could be employed to provide the valve 166, such as described herein.

By way of further example, prior to implanting the system 150 in the left ventricle 153, the dilated mitral annulus can be forced to a reduced diameter. For instance, the mitral annulus can be reduced by applying a purse-string suture around the mitral annulus and closing the purse-string suture to a desired diameter, such as corresponding to the diameter of the valve 166 that is to be implanted. The annulus of the inflow valve 166 can then be sutured to the mitral annulus 155, such as shown in FIG. 4. The outflow end of the outflow portion 160 further can be sutured to the sidewall of the aorta 157 to maintain the outflow portion at a desired position relative to the aorta (e.g., at the base of the aorta).

The chamber of the pouch 152 implanted in the dilated ventricle 153 simulates the function of a normal ventricle. That is, the pouch 152 operates to limit the volume of blood within the ventricle since the pouch has a reduced cross-section relative to the patient's dilated ventricle. Consistent with La Place's law, blood can be more easily (e.g. less exertion from cardiac muscle 163) pumped from the chamber of the system 150 than from the patient's native dilated ventricle. That is, the system 150 provides a chamber having a reduced volume relative to the volume of the dilated ventricle, such that less energy and reduced contraction by the associated cardiac muscle 163 are required to expel a volume of blood at a suitable pressure from the pouch 152.

Portions of the sidewall of the system 150 further can be secured relative to the cardiac muscle 163, such as by employing strips 165 of a suitable biocompatible tissue to tether various parts of the sidewall 168 relative to the surrounding cardiac muscle. The strips 165 can help hold the pouch 152 in a desired shape relative to the dilated ventricle 153 during contractions of the cardiac muscle 163. After or during implantation, blood and other fluid in the pouch 152 can be removed from around the system 150 to enable the heart 151 to return to a more normal size. In such a situation, the strips 165 of tissue may remain, but typically will become less functional since their tethering function is reduced after the heart returns to a more normal size.

FIG. 5 depicts the system 150 being implanted in combination with an aortic valve 171 according to an aspect of the present invention, in which the same reference numbers refer to the same parts identified with respect to FIG. 4. In FIG. 5, an additional valve 171 is attached at the outflow annulus 164 of the outflow portion 160. As described herein, various types of valves can be employed at the aortic position. FIG. 5 and FIG. 6 provide but two examples of numerous different types of valves that can be utilized.

In the example of FIG. 5, the valve 171 can be implanted at the aortic position according to a generally sutureless method of implantation ("sutureless" meaning that sutures are not required, but sutures can still be used), such as shown and described in co-pending U.S. patent application Ser. No. 10/778,278, which was filed on Feb. 13, 2004, and which is incorporated herein by reference. The outflow valve 171 typically will be implanted after the outflow portion 160 of the system 150 has been attached to the aorta 157 (e.g., by continuous sutures through an opening made in the aorta).

Additionally, prior to implanting the valve 171, the patient's own aortic valve or at least calcified portions thereof should be removed.

As shown in FIG. 5, the valve 171 is being implanted through an opening in the patient's aorta 157. The valve 171 includes an inflow end 173 that is positioned at the aortic annulus 159, with an outflow end 175 of the prosthesis extending into the aorta 157. As mentioned above, the implantation can be considered sutureless since the valve 171 includes spikes or other projections 177 that extend radially outwardly from the exterior part of the valve.

In the example of FIG. 5, the spikes 177 are arranged as sets of fingers that extend arcuately toward each other in substantially opposite directions so as to form a clamp-like structure. Additionally, the respective sets of opposing fingers can be arranged in a generally circular array circumferentially about a base portion of the valve 171 proximal the inflow 173 end thereof. For example, each adjacent pairs of fingers alternate In first and second axial directions with one another and are spaced circumferentially apart along the base portion of the valve 171. The ends of the spikes 177 can also be sharpened to facilitate their insertion into the tissue at the aortic annulus 159.

The spikes 177 can be constructed of a resilient material, such as a metal or plastic. A generally resilient material should be sufficiently elastic to permit the spikes 177 to be deformed from an original first condition, extending outwardly to form the clamp-like structure, to a second condition. In the second condition, the sets of spikes 177 are oriented substantially linearly and generally parallel with the longitudinal axis of the valve (but in opposite directions relative to the base portion), and be capable of returning substantially to their original first condition. The valve 171 is carried within an implanter 179 that holds the spikes in the second condition to facilitate positioning of the valve at the aortic annulus 159. The implanter can be of the type shown and described in the above-incorporated application Ser. No. 10/778,278, although other types of implanters could also be utilized.

By way of further example, the implanter 179 can be inserted through an incision in the aorta 157, such as part of an aortotomy procedure (e.g., a transverse aortotomy) while the patient is on cardiopulmonary bypass. The implanter 179 can be employed to position the distal end of the cylindrical member at a desired location relative to the annulus 159. Once at the desired position, the valve can be discharged from the implanter 179, such that an inflow set of spikes 177 return toward their original shape to penetrate into the surrounding tissue at the annulus 159 tissue. After the remaining length of the prosthesis is discharged, an outflow set of the spikes 177 are also released to return toward their original shape to penetrate into the annulus 159 tissue (e.g., the first condition as shown in FIG. 5).

In the implanted position, an outflow portion 181 of the valve 171 thus extends axially into the aorta 157, with the respective sets of spikes 177 cooperating to inhibit axial as well as rotational movement of the valve relative to the aortic annulus 159. Additionally, lobes (or outflow valve extensions) 183 extending from the outflow commissures of the valve can be attached to the sidewall of the aorta 157, such as by sutures 185. By attaching the lobes 183 to the aorta 157, improved valve competence and coaptation can be achieved, and prolapse can be mitigated.

In order to facilitate loading the valve 171 into the implanter 179, the implanter can include a retaining mechanism 187. The retaining mechanism 187 can be in the form of a retaining ring dimensioned and configured to slide along the exterior of the valve 171. In the example of FIG. 5, the implanter includes a guide system 191 operative to move the retaining mechanism 187 for repositioning the spikes 177 to the second condition. A number of connecting elements (e.g., sutures) connect to the retaining mechanism 187, so that the retaining mechanism may move commensurately with axial movement of the guide system 191.

The valve 171 can also include a covering 189 of a biocompatible material connected for movement with the spikes, such as by connected by sutures (not shown). The covering 258 can be implemented as a pair of generally annular sheet (one for the inflow set of spikes and one for the set of outflow spikes) that move as a function of the movement of the spikes 177.

Additionally, to facilitate implantation of the pouch 152 within the ventricle 153, a vacuum assembly or pump 195 can be employed to remove fluid from the patient's dilated ventricle. Those skilled in the art will understand and appreciate various types of pump devices that could be utilized. The pump 195 can include one or more nozzles or other members 197 fluidly connected with the pump for removing the blood from the ventricle 153. By removing the blood from the dilated ventricle 153, self-remodeling of the cardiac muscle to a more normal size is facilitated.

FIG. 6 depicts yet another example of a system 200 implanted for improving ventricular function of a heart 202. The system of FIG. 6 is similar to that shown and described in FIG. 5, but different types and configurations of biological heart valves 204 and 206 are utilized at the mitral annulus 208 and aortic annulus 210, respectively. In the particular example of FIG. 6, a sutureless type of valve 204 is implanted at the mitral annulus 208 and a more conventional type of biological heart valve prosthesis 206 is employed at the aortic annulus 210. While the examples of FIG. 6 depict biological heart valve prostheses being employed at aortic and mitral positions, those skilled in the art will understand and appreciate that other types of valves (e.g., mechanical, biological, bio-mechanical) can also be utilized. That is, as described herein, any type of valve can be provided at either of the position according to an aspect of the present invention, and the valves at the respective positions can be the same or different types of valves.

By way of further example, the dilated, insufficient pulmonic valve (or at least calcified portions) thereof should be removed from the mitral annulus 208 prior to implanting the valve 204. The valve 204 is attached to a pouch 212 configured to simulate a substantially normal ventricle. The pouch is positioned within the ventricle, such as shown in FIG. 6. To attach the valve 204 at the annulus 208, an inflow end 214 of the valve is annularized with respect to the annulus 208. The positioning and implantation of the valve 204 can be implemented employing an implanter, such as described herein with respect to FIG. 5 and the above-incorporated application Ser. No. 10/778,278. In one approach, the system 200, including the valve 204 can be positioned into the ventricle 216 of the heart 202 through an incision made in the apex 218 of the heart 202.

The valve 204 can be substantially the same as the valve 171 shown and described with respect to FIG. 5. Accordingly, details of such valve have been omitted from the description of FIG. 6 for sake of brevity, and since reference can be made to FIG. 5. Once at the desired position, the valve 204 can be discharged from the implanter, such that an the opposed spikes 220 can return to their normal clamp-like condition and penetrate into the annulus 208 tissue. The respective sets of spikes 220 thus cooperate to anchor the valve 204 relative to the annulus 208 (e.g., clamping onto the tissue at the annulus) so as to inhibit axial and rotational movement of the valve.

In the implanted position, an outflow portion 222 of the valve 204 thus extends axially into the chamber defined by the pouch 212, which is located within the ventricle 216. Additionally, the outflow portion 222 of the valve can be sutured or otherwise secured to the sidewall of the pouch 212 proximal the inflow annulus thereof. As described herein, the valve 204 can be stented or unstented.

The outflow valve 206 can be any type of valve, such as a biological valve depicted in FIG. 6. The valve 206 can be implanted through an incision in the aorta 230, such as after the pouch 212 and the valve 204 have been mounted in the heart 202. For instance, the tubular branch 232 extending from the sidewall of the pouch can be secured (e.g., by continuous sutures) to the base of the aorta 230. Then the valve can be positioned at the aortic annulus and implanted to provide for substantially unidirectional flow of blood from the pouch 212 and into the aorta through the valve 206. The incision in the aorta 230 can then be closed in a desired manner.

The interstitial space in the ventricle 216 between the pouch 212 and the cardiac muscle 234 will reduce over time, enabling the heart to self-remodel and function more normally. The remodeling can be facilitated by removing surrounding fluid, such as via suction device, as depicted with respect to FIG. 5. Those skilled in the art will understand and appreciate that any type of valves can be employed at either of the aortic and mitral positions, and that the valves depicted herein are for purposes of illustration and not by way of limitation.

In view of the foregoing, those skilled in the art will understand and appreciate that the approach described above with respect to FIGS. 5 and 6 can be employed significantly improve ventricular function.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A method for improving ventricular function of a heart, comprising:
    implanting a pouch in a ventricle, the pouch including an inflow annulus;
    mounting an inflow valve associated with the inflow annulus of the pouch at a mitral position to provide for substantially unidirectional flow of blood through the inflow valve and into the implanted pouch;
    securing an outflow end portion of a generally cylindrical member at an aortic annulus, the generally cylindrical member extending from a sidewall of the pouch and terminating in the outflow end portion to provide fluid communication from within the pouch into an aorta; and
    removing fluid from a space in the ventricle between the pouch and surrounding cardiac tissue to facilitate self-remodeling of the heart, the fluid being in direct contact with the pouch and the surrounding cardiac tissue.

2. The method of claim 1, further comprising mounting an outflow valve to provide from substantially unidirectional flow of blood from the pouch into the aorta.

3. The method of claim 1, further comprising connecting a length of at least one tether between an exterior of the sidewall of the pouch and surrounding cardiac muscle to help maintain a desired configuration of the pouch.

4. The method of claim 1, wherein the pouch is formed of a natural tissue material.

5. A system for improving ventricular function of a patient's heart, comprising:
    means for limiting a volume of blood received within an enlarged ventricle of the patient's heart, the means for limiting being formed of a natural tissue material;
    means for providing for substantially unidirectional flow of blood into the means for limiting; and
    means for providing for substantially unidirectional flow of blood out of the means for limiting into an aorta of the patient's heart; and
    means for tethering a portion of the means for limiting relative to cardiac muscle of the patient's heart so as to maintain a desired configuration of the means for limiting, the means for tethering comprising at least one strip of a biological material.

* * * * *